(12) United States Patent
Junio et al.

(10) Patent No.: US 12,295,762 B2
(45) Date of Patent: *May 13, 2025

(54) METHOD FOR VERIFYING HARD TISSUE LOCATION USING IMPLANT IMAGING

(71) Applicant: Mazor Robotics Ltd., Caesarea (IL)

(72) Inventors: Dany Junio, Brookline, MA (US); Eli Zehavi, Tel Aviv (IL)

(73) Assignee: Mazor Robotics Ltd., Caesarea (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/393,365

(22) Filed: Dec. 21, 2023

(65) Prior Publication Data
US 2024/0122560 A1    Apr. 18, 2024

Related U.S. Application Data

(63) Continuation of application No. 16/765,930, filed as application No. PCT/IL2018/051274 on Nov. 22, 2018, now Pat. No. 11,864,934.
(Continued)

(51) Int. Cl.
*A61B 6/12*    (2006.01)
*A61B 34/10*   (2016.01)
(Continued)

(52) U.S. Cl.
CPC .............. *A61B 6/12* (2013.01); *A61B 34/10* (2016.02); *A61B 90/03* (2016.02); *A61B 90/37* (2016.02);
(Continued)

(58) Field of Classification Search
CPC ........... A61B 6/12; A61B 34/10; A61B 90/37; A61B 2034/102; A61B 2034/105;
(Continued)

(56) References Cited

U.S. PATENT DOCUMENTS 5,772,594 A    6/1998   Barrick
6,301,495 B1   10/2001  Gueziec et al.
(Continued)

FOREIGN PATENT DOCUMENTS

CN    102300512    12/2011
CN    103961130    8/2014
(Continued)

OTHER PUBLICATIONS

West et al. "Fiducial point placement and the accuracy of point-based, rigid body registration," Neurosurgery, Apr. 2001, vol. 48, No. 4, pp. 810-817.
(Continued)

*Primary Examiner* — Michelle Chin
(74) *Attorney, Agent, or Firm* — Sheridan Ross P.C.

(57) ABSTRACT

A low radiation, intra-operative method using two-dimensional imaging to register the positions of surgical implants relative to their pre-operative planned positions. Intraoperatively, a pair of two-dimensional fluoroscope images in different planes or a single three-dimensional image is acquired and compared to a set of three-dimensional preoperative images, to allow registration of the implant region anatomy. A second set of intraoperative fluoroscope images is acquired of the surgical area with implants in place. The second set of images is compared with the first set of intraoperative images to ascertain alignment of the implants. Registration between first and second intraoperative image sets is accomplished using the implants themselves as fiducial markers, and the process repeated until an acceptable configuration of the implants is obtained. The method is particularly advantageous for spinal surgery.

20 Claims, 3 Drawing Sheets

Related U.S. Application Data

(60) Provisional application No. 62/589,572, filed on Nov. 22, 2017.

(51) Int. Cl.
*A61B 90/00* (2016.01)
*G06V 10/75* (2022.01)

(52) U.S. Cl.
CPC .... *G06V 10/7515* (2022.01); *A61B 2034/102* (2016.02); *A61B 2034/105* (2016.02); *A61B 2090/363* (2016.02); *A61B 2090/364* (2016.02); *A61B 2090/374* (2016.02); *A61B 2090/3762* (2016.02); *A61B 2090/3966* (2016.02)

(58) Field of Classification Search
CPC ........ A61B 2090/363; A61B 2090/364; A61B 2090/374; A61B 2090/3762; A61B 2090/3966
See application file for complete search history.

(56) References Cited

U.S. PATENT DOCUMENTS

| | | | |
|---|---|---|---|
| 6,477,400 | B1 | 11/2002 | Barrick |
| 9,308,050 | B2 | 4/2016 | Kostrzewski et al. |
| 11,864,934 | B2 | 1/2024 | Junio et al. |
| 2004/0171924 | A1 | 9/2004 | Mire et al. |
| 2004/0215071 | A1 | 10/2004 | Frank et al. |
| 2005/0203384 | A1* | 9/2005 | Sati .................. G06F 3/017 600/426 |
| 2008/0269596 | A1* | 10/2008 | Revie ................ A61B 90/39 705/28 |
| 2009/0177081 | A1 | 7/2009 | Joskowicz et al. |
| 2009/0209851 | A1 | 8/2009 | Blau |
| 2014/0267255 | A1 | 9/2014 | Graumann et al. |
| 2014/0324182 | A1 | 10/2014 | Graumann et al. |
| 2014/0334709 | A1 | 11/2014 | Siewerdsen et al. |
| 2015/0030236 | A1 | 1/2015 | Wilson et al. |
| 2015/0150523 | A1 | 6/2015 | Sirpad et al. |
| 2017/0165008 | A1 | 6/2017 | Finley |
| 2017/0340389 | A1 | 11/2017 | Otto et al. |
| 2017/0367738 | A1 | 12/2017 | Scholl et al. |
| 2019/0371474 | A1 | 12/2019 | Borsic |

FOREIGN PATENT DOCUMENTS

| | | |
|---|---|---|
| CN | 107072719 | 8/2017 |
| CN | 107205691 | 9/2017 |
| EP | 3113710 | 1/2017 |
| WO | WO 2005/081863 | 9/2005 |
| WO | WO 2009/087214 | 7/2009 |
| WO | WO 2013/175471 | 11/2013 |
| WO | WO 2017/158592 | 9/2017 |

OTHER PUBLICATIONS

International Search Report and Written Opinion prepared by the Israel Patent Office on Feb. 21, 2019, for International Application No. PCT/IL2018/051274.
Official Action with English Translation for China Patent Application No. 201880074930.8, dated Sep. 20, 2023, 15 pages.
Extended Search Report for European Patent Application No. 18881739.9, dated Nov. 22, 2021, 7 pages.
Official Action for U.S. Appl. No. 16/765,930, dated Sep. 1, 2022 17 pages.
Official Action for U.S. Appl. No. 16/765,930, dated Feb. 13, 2023 20 pages.
Official Action for U.S. Appl. No. 16/765,930, dated May 10, 2023 21 pages.
Notice of Allowance for U.S. Appl. No. 16/765,930, dated Sep. 1, 2023 9 pages.

* cited by examiner

METHOD FOR VERIFYING HARD TISSUE LOCATION USING IMPLANT IMAGING

CROSS-REFERENCE TO RELATED APPLICATIONS

This application is a continuation of U.S. patent application Ser. No. 16/765,930, filed on 21 May 2020, which is a national stage application under 35 U.S.C. 371 and claims the benefit of PCT Application No. PCT/IL2018/051274 having an international filing date of 22 Nov. 2018, which designated the United States, which PCT application claimed the benefit of U.S. Provisional Patent Application No. 62/589,572, filed on 22 Nov. 2017, the entire disclosures of each of which are incorporated herein by reference.

FIELD OF THE INVENTION

The present invention relates to the field of orthopedic surgery, especially relating to correctly maintaining positional information of tissue using the images of implants.

BACKGROUND

The current state of the art in spinal instrumentation for vertebral alignment does not readily enable the surgeon to visualize the alignment of the patient's spine in real time. Existing options for verifying the accuracy of placement of screws, rods or other implants during the surgical procedure include direct intra-operative visualization by the surgeon; fluoroscopy images which often have a large margin of clinical error; and intra-operative 3D CT images that are of high quality but have several disadvantages, primarily a high patient radiation dose, which can be many times the levels of radiation from a simple fluoroscopic image. The process of repeatedly bringing the CT scanner into the operating room and performing the scan also significantly lengthens the operative procedure, which may have negative repercussions on the patient's recovery time. Furthermore, the cost of the operation increases with longer use of the operating room. For all of these reasons, it is less practical to perform 3D scans repeatedly during an operation. These drawbacks point to the need for a quick, higher accuracy and low-radiation means of providing real-time feedback to the surgeon on the progress and success of the operative treatment using quantitative intra-operative values such as spinal alignment parameters.

In an imaging registration-based procedure, the surgeon performs registration of the surgical area using fluoroscopy or intraoperative 3-D imaging with the preoperative 3-D images, such as CT or MRI image sets. Subsequent shifts and rotations to the patient's surgically-registered anatomy, such as the vertebrae during spine surgery, compromise the registration and therefore reduce the accuracy of the alignment. Thus, the induced accuracy of, for example, insertion of interbody spacers between vertebrae during a spinal fusion procedure, is likewise reduced. Such motion potentially affects both navigation systems and systems for the accurate positioning of mechanical surgical arms.

The uncertainty inherent in surgical procedures lacking direct vision of the three-dimensional location of inserted implants results in doubt regarding the success of the vertebral fusion operation on the part of both surgeon and patient. In surgical procedures to correct scoliosis, kyphosis or other spinal deformity, high levels of stress may be placed on the rods and screws in the process of correcting the alignment of the bony anatomy. Such stress on the spinal column may cause a pedicle screw to pull out, becoming detached from the vertebra. Detachment of a pedicle screw leaves the attached rod less effective or even ineffective in correcting the deformity or instability it was designed to repair. Such a detachment may pass unnoticed by the surgeon until follow up post-operative scans are obtained. The above-mentioned limitations thus indicate a need to provide the surgeon with a simpler intraoperative method of registration of the surgical site, in order to overcome inaccuracies which may arise from prior art registration procedures because of motion of the patient, or motion generated by manipulation of the spine by the surgeon. Such a method should be able to optimize surgical results, and specifically to provide information of the exact location of implants within a bony structure.

Prior art examples in this field have attempted to improve accuracy of three-dimensional placement of surgical implants. For example, the use of fiducial points is described in "Fiducial point placement and the accuracy of point-based, rigid body registration" by West et al., Neurosurgery. 2001 April; 48(4):810-6. U.S. Pat. No. 9,308,050 to Kostrzewski et al. entitled "Robotic system and method for spinal and other surgeries" discloses software and a robotic measurement system for screw placement. It uses an external tracking system to perform the registration procedure. U.S. Pat. No. 5,772,594 to Barrick discloses "Fluoroscopic image-guided orthopedic surgery system with intraoperative registration". This system also uses external fiducial markers comprised of LEDs and pins for registration. As noted, external markers may shift during the procedure, resulting in misalignment of the patient's actual anatomy with the medical images on which the preoperative surgical plan was prepared.

US patent application publishes as US 2017/0367738 to Scholl et al. discloses "Systems and methods for planning, performing, and assessing spinal correction during surgery", which describes a customized, rod-bending software program. WO 2005/081863 to Pacheco discloses a "Method for improving pedicle screw placement in spinal surgery", and provides quantitative measurements of vertebral anatomy to determine ideal pedicle screw diameter, length and trajectory.

There therefore exists a need for an intraoperative system for performing simple intraoperative registration with preoperative images and pre-surgical planning, which overcomes at least some of the disadvantages of prior art systems and methods, such that the alignment of implants may be more accurately determined intraoperatively.

The disclosures of each of the publications mentioned in this section and in other sections of the specification, are hereby incorporated by reference, each in its entirety.

SUMMARY

The present disclosure describes new exemplary systems for a simple, low-radiation, intra-operative method to register the current positions of surgical implants relative to their intended positions according to a pre-operative surgical plan, to assist the surgeon to quantify the success of an inserted implant when compared to the computer-assisted preoperative surgical plan. The method of the present disclosure relates to orthopedic procedures for bone manipulation or stabilization using registration of preoperative images of the surgical area upon which the images of implants to be used in a planned surgical procedure has been superimposed, with intraoperative images of the surgical area as the procedure, is being carried out.

Preoperative 3-D images, such as CT or MRI scans, are acquired of the operative region of the spine to allow pre-surgical planning of an operative procedure. The pre-surgical planning enables the surgeon to decide the location and position of implant instrumentation, such as rods, vertebral interbodies and pedicle screws in spinal stabilization, or different types of hardware in various other orthopedic procedures. The location of these implants in the intraoperative images is superimposed on the preoperative images, and the surgeon maps the operation using a conveniently available surgical planning software. The plan may include, in this instance, manipulation of the vertebrae of the spine, as needed to stabilize or correct abnormal spinal curvatures or vertebral misalignment. Because such manipulation may necessitate a change in position, alignment or rotation of vertebrae intraoperatively, the exact location of pedicle screws or other implants at a given point of the surgical procedure may not correspond exactly to the intended position in the preoperative plan. Furthermore, such manipulation of the spine may place stress on the bone-implant system as a curvature abnormality is corrected. For this reason, intraoperative verification of implant positioning is necessary both to verify that the implants have been inserted according to surgical plan, and furthermore, to ensure that the pedicle screws and other implants are correctly inserted. Such determination is difficult to make using direct visualization, and thus radiologic solutions are useful to image the bone-implant system.

At the start of the operation, an initial pair of fluoroscope images in anterior-posterior and lateral views is obtained of the patient on the operating table, to verify that the patient's bony anatomy aligns with the preoperative images. The registration for this step comparing intraoperative images with the preoperative plan is accomplished using patient-specific bony landmarks or other radio-dense anatomical features. After initial placement of the pedicle screws, a second intra-operative fluoroscopy procedure is carried out to assist the surgeon to register the patient's anatomy, as observed on the current intraoperative images, with the pre-operative 3D images. The second set of intraoperative fluoroscope images may be once again a pair of anterior-posterior and lateral views of the operative area. The registration for these images is based on the three-dimensional position of the pedicle screws or other implants relative to those in the preoperative plan. A computer-executed algorithm, or manual inspection on an interactive monitor showing the surgical plan, can identify the spatial location of radio-dense objects such as pedicle screws, and compare that location with the preplanned positions. This registration procedure provides high-fidelity alignment of the implants as they are being introduced into the patient, even in situations where the position of the patient, or the patient's bone structure, may have shifted from its position determined during initial registration at the commencement of surgery. Because the alignment is provided by intrinsic, radiopaque elements of the bone-implant system, rather than by external reference markers, e.g., on the patient's skin, or temporary internal fiducials, it is not dependent on elements that may shift during manipulation of the subject's bony anatomy, thus providing a means for improved accuracy of the registration procedure.

Further intraoperative images, generally taken by fluoroscopy, can be repeatedly generated after successive surgical manipulations on the subject's skeletal anatomy. Surgical manipulations are generally carried out according to the surgical plan, which aims to correct spinal alignment parameters, unintended vertebral relative motion while inserting vertebral interbodies, and similar processes. Because these manipulations alter the position of implants and the bones into which they are inserted, further registration algorithms can be used and may be needed to indicate any insertion spatial error, by comparing each generated intra-operative image set to a previously registered image sequence.

After this procedure has been performed and radio-dense objects in the fluoroscopy images have been compared to their intended location in their preplanned position, an iterative process can be used to improve or correct the implant location using registration between sequential sets of fluoroscopic image pairs. In addition to the improved accuracy of this registration process, another advantage is that it does not require intraoperative three-dimensional imaging, thus saving significant operating room time and patient and staff exposure to radiation.

One exemplary implementation of such a process can include the following steps:
(i) acquiring an image of the currently operated area;
(ii) virtually performing a process of automatic or manual matching between the recently inserted radiodense objects, e.g. pedicle screws, and the surgical plan images, wherein the radiodense objects can be aligned using an automatic algorithm or a manual user marking on-screen;
(iii) verifying that registration is current vis-à-vis the patient anatomical position, such as the corrected values of spinal alignment parameters, the vertebral relative motion while inserting interbodies, and similar processes;
(iv) manipulating the anatomical alignment of the patient's spine;
(v) acquiring two images (of a 2-D imaging modality) or a single 3-D image of the implants in the surgical site;
(vi) performing registration between the previous and current intraoperative images using the location of radiodense implants;
(vii) providing information regarding any undesired change in the relative position of inserted implants, such as would arise from pedicle screw pull-out; and
(vii) repeating steps (i)-(vi) as needed to achieve an acceptable implant configuration.

Versions of the method described herein may be applied to many types of surgical operations. In some implementations, the method may be used to verify the position of pedicle or other screws used to attached a plate or rod to a bone or adjacent bones needing stabilization or fusion. In this case, the registration procedure of the present application is primarily for the purpose of verification that the implants are in the correct location. In other implementations, the method may be used as a more integral part of the surgical procedure to correct a bone misalignment, such as a broken bone or a scoliotic spine, such that the preoperative plan includes a positive step or steps to manipulate or re-align the operated bone or bones. In such cases, the registration procedure is used to verify the initial placement of one or more implant components, after which the bone is brought into alignment. The registration procedure would be performed as many times as needed to ensure both that the final alignment of the bone is according to the surgical plan, and that any deviations from the surgical plan have been detected and corrected according to the surgeon's decision.

There is thus provided in accordance with exemplary implementations described in this disclosure, a method for registration of intraoperative images of a surgical site of a subject to a surgical plan generated preoperatively, showing the planned position of implants on images of the surgical site of the subject, comprising:
  (a) acquiring a three dimensional set of preoperative images of at least the surgical site to which the surgical plan relates,
  (b) acquiring a first set of intraoperative images of the surgical site,
  (c) registering the first set of intraoperative images with the preoperative image set showing the planned position of implants, such that the planned position of implants is virtually imposed on the first set of intraoperative images,
  (d) acquiring a second set of at least one intraoperative image showing the position of previously inserted implants,
  (e) registering the second set of at least one intraoperative image showing the previously inserted implants from step (d) with the first at least one intraoperative image from step (c) using the previously inserted implants as fiducial markers,
  (f) verifying the position according to the preoperative surgical plan of the previously inserted implants in further intraoperative images, using the image registration from step (e), and
  (g) repeating at least some of steps (d) to (f) until the pre-surgical plan is achieved.

In such a method, the surgical site may be a region of the spine, and the fiducial markers may be comprised of pedicle screws, intervertebral connection rods, vertebral interbodies, or any three-dimensional, radio-dense implant. Fiducial markers may also be radiodense staples.

Furthermore, the bone to be instrumented may be a bony region of the subject, which may be other than the spine. Preoperative images may be some or all of a set of three-dimensional images acquired by at least one of CT and MRI, or a set of two-dimensional x-ray images of the patient in various positions of bending, such as flexion, extension, lateral bending or axial rotation.

The intraoperative images may comprise a pair of anterior-posterior and lateral views acquired by fluoroscopy, or a single three-dimensional image acquired by CT-fluoroscopy.

According to yet other implementations of the present disclosure, there is further provided a method of image registration that may be used in conjunction with a spinal or any other bone fusion procedure, for registration of preoperative images showing a surgical plan for implant insertion, to intraoperative images, the method comprising:
  (a) acquiring a three dimensional set of preoperative images of at least a surgical site to which the surgical plan relates,
  (b) acquiring a first at least one intraoperative image of the surgical site,
  (c) registering the first at least one intraoperative image with the preoperative image set showing the position of planned implants,
  (d) inserting the implants according to the surgical plan,
  (e) acquiring a second at least one intraoperative image showing the inserted implants,
  (f) registering the second at least one intraoperative image from step (e) with the registered first intraoperative image from step (c), using the implants as fiducial markers,
  (g) verifying the position of the implants according to the surgical plan,
  (h) if implants are not positioned according to the surgical plan, performing an adjustment on elements at the surgical site,
  (i) obtaining a third at least one intraoperative image,
  (j) registering the third intraoperative image from step (i) with the second intraoperative image from step (f), using inserted implants as fiducial markers; and
  (k) repeating at least some of steps (g) through (j) until the positions of the implants matches the surgical plan.

Such methods may further be used in combination with a spinal manipulation procedure, for registration of preoperative images, showing a surgical plan for implant insertion and correction of misaligned bones, to intraoperative images, the method comprising:
  (a) acquiring a three dimensional set of preoperative images of at least the surgical site to which the surgical plan relates,
  (b) acquiring a first at least one intraoperative image of the surgical site,
  (c) registering the first at least one intraoperative image with the set of preoperative images showing the planned position of implants,
  (d) inserting the implants according to the surgical plan,
  (e) acquiring a second at least one intraoperative image showing the implants,
  (f) registering the second at least one intraoperative image from step (e) with the registered first intraoperative image from step (c), using inserted implants as fiducial markers,
  (g) verifying the position of inserted implants according to the surgical plan,
  (h) performing a manipulation of the surgical site according to the surgical plan to bring spinal parameters into alignment,
  (i) obtaining a third at least one intraoperative image,
  (j) registering the third intraoperative image from step (i) with at least one of the previous intraoperative images from step (f) and first intraoperative image from step (c), using inserted implants as fiducial markers, and
  (k) repeating at least some of steps (g) through (j) until the position of implants matches the surgical plan.

BRIEF DESCRIPTION OF THE DRAWINGS

The present invention will be understood and appreciated more fully from the following detailed description, taken in conjunction with the drawings in which.

DETAILED DESCRIPTION

Figure 1:
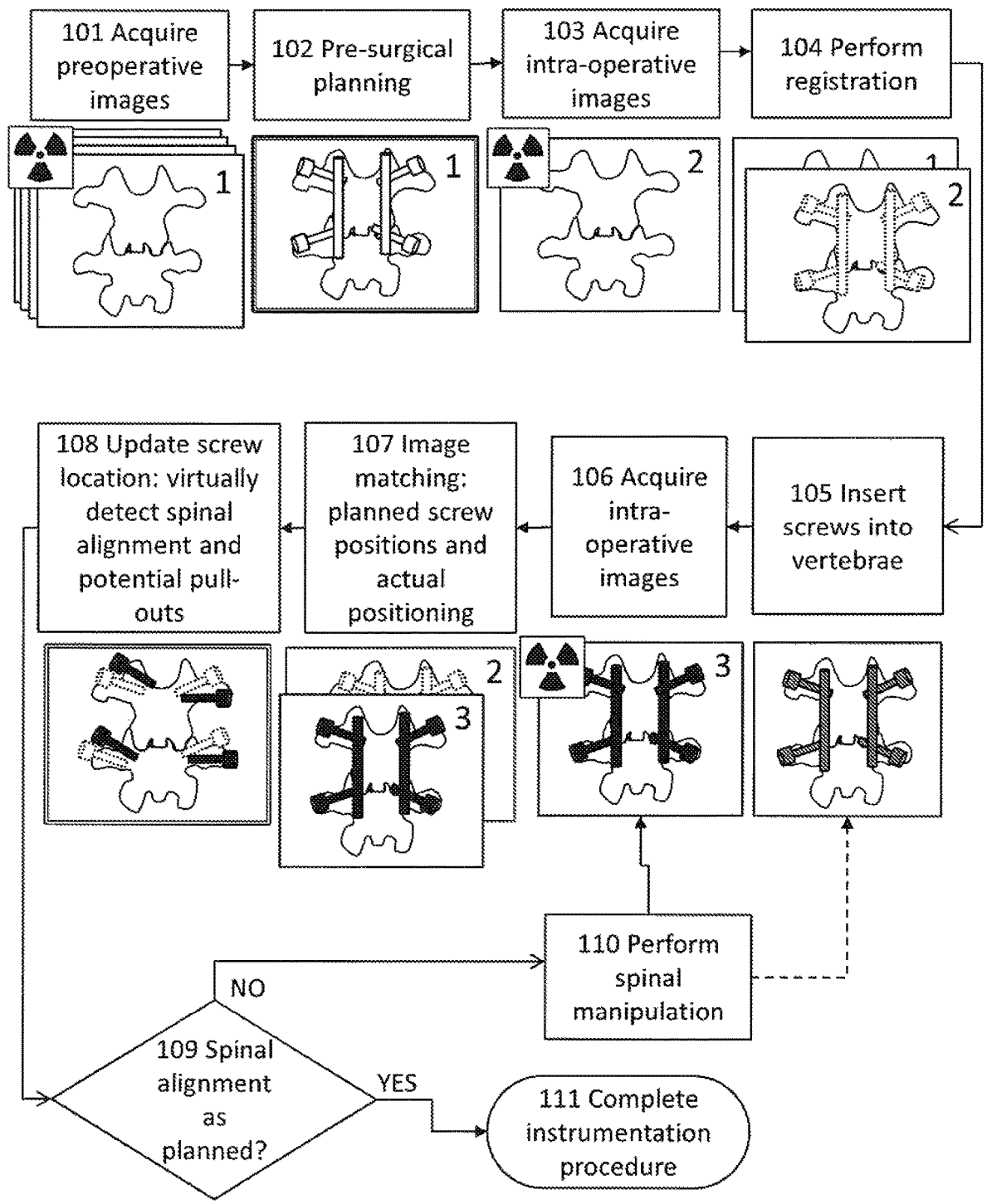
FIG. 1 shows an overview of the method with sequential steps illustrated.

Reference is now made to FIG. 1, which illustrates schematically an overview of one exemplary implementation of the method. Sequential steps are shown, beginning with step 101, which shows the acquisition of a 3-dimensional set of preoperative medical images of the region of surgical interest, the set being marked 1. Such medical images may be CT, MRI, or a series of fluoroscopic images to provide a three-dimensional set of the operative region of interest. In this application, the example of a vertebral fusion operation, using two fusion rods and four pedicle screws, is used to illustrate the method, but it is to be understood that the method is applicable for surgery on any suitable part of the subject's anatomy. The radiation sign in the drawings at any step indicates the taking of X-ray images.

Using these medical images, surgical planning is performed, as shown in step 102, where there is shown the example of a pair of vertebrae connected by a pair of fusion rods each of which is attached to its vertebrae by means of pedicle screws. As mentioned, the implants need not be pedicle screws, but could be radiopaque implants anywhere else in the subject's anatomy. The output of the pre-surgical planning comprises details of the selected implants, including, for instance, at least some of the number, length, diameter, and composition of the rods, and some of the size, length, number and pose of the pedicle screws.

In step 103, a set of images, marked set 2, is generated intraoperatively, these images generally being a pair of two-dimensional X-ray fluoroscopic images in two planes, to provide three-dimensional information. Such images, while being simple and fast to generate, and involving limited radiation, do not show the anatomic features as well as CT images, such that the accuracy of any decisions taken on the basis of such intraoperative fluoroscope images, may be limited. Likewise, the accuracy of any registration performed using anatomical details obtained from those intraoperative fluoroscope images may also be of more limited accuracy.

In step 104, a virtual registration is performed of the preoperative images (set 1) from step 101, which are accurate and have high resolution, with the intraoperative images (set 2), of limited accuracy and resolution, from step 103. The purpose of this registration procedure is to provide detailed information in three dimensions of the surgical area, which is not available under direct visualization during the surgical procedure. This registration is illustrated in the drawing by the superposition of the preoperatively defined surgical plan implanted on the preoperative 3D image set 1, with the intraoperative image 2, acquired in step 103. The position intended according to the surgical plan, of the implants from preoperative image set 1, are therefore now indicated on the intraoperatively generated fluoroscope image or images, marked 2. The registration can be performed using an automatic image processing algorithm, or by manual marking on a screen of features to be compared between the images being registered.

Step 105 represents the surgical insertion of implants into the operation site, according to the surgical plan as shown on the registered images obtained in steps 103-104. The information regarding implant placement from the pre-surgical planning is then transferred to the new set of images. Any deviations in the patient's physical alignment are now able to be corrected according to the registration.

In step 106, after placement of the implants, a further intraoperative medical image (marked 3) is obtained in order to ascertain the actual positioning of the implants. This image set then serves as the baseline reference image set, with the inserted implants now serving as fiducial markers for any further intraoperative images. Such a baseline image set is used in order to define any further motion of the implant set following the initial surgical implantation in step 105.

In step 107, a further registration step is performed in which the initial registered set of intra-operative images obtained in step 104 (set 2), incorporating the surgically planned positions of the implants inserted into the preoperative set of images, is aligned and registered with the follow-up baseline set of intra-operative images (set 3) obtained in step 106, using the implanted pedicle screws or their associated rods as fiduciary markers. As used in this disclosure, a fiduciary marker is an object, in this case the implanted pedicle screws and/or their associated rods, placed in the field of view of an imaging system which appears in the image produced, for use as a point of reference or a measure for defining the imaged position and orientation. Step 107 therefore embodies an important advantage of the present method, in that the implanted elements, which, because of their highly radiopaque nature, have a distinct and well-defined rendering in fluoroscopic images, can be used as fiduciary elements for accurately registering successively obtained intraoperative images, with an image (marked 3) which incorporates the present implant configuration in a high resolution image modality. These fiduciary markers obviate the need for external reference markers, which may shift as the patient is moved during the spinal manipulation shown in step 108 and step 204 of FIG. 2. A further advantage of this method is that a pair of two-dimensional fluoroscopic images using these internal fiduciary markers provides the three dimensional information needed for the registration procedure much more simply than the use of a complex 3-D imager intraoperatively.

Once the above referenced registered images in steps 106 and 107 have been obtained, any subsequent movements of the subject's anatomy or of the implants therein, can then be readily and accurately obtained using further simple X-ray fluoroscopic images. Thus, if the surgeon needs to adjust the position of a vertebra (in the example shown in FIG. 1), or to manipulate any more extensive region of the patient's anatomy, one or more further fluoroscope images can be taken, and the clearly defined positions of the implants can be compared with the baseline images obtained in steps 106-107, and any unintended deviation in position or orientation of the implants can be readily ascertained. Detection of deviation is particularly important for determining if implant motion or detachment has occurred, as may occur during surgical manipulation of the subject's spine or of the fusion rods. This is illustrated in step 108, and in more detail in FIG. 2, where the spinal alignment after such manipulation is determined, and any unintentional misalignment or even pull-out of the pedicle screws can be identified.

Information on deviation or misplacement of the implant is then used to determine, in step 109, if the spinal alignment and pedicle screw position is according to the preoperative planning. If so, the instrumentation procedure is completed, as in step 111. If not, the surgeon may need to perform additional spinal or rod manipulation, as shown in step 110, and may even decide to return to step 105 to perform adjusting, removing, or replacing one or more pedicle screws. These steps are followed by repetition of the fluoroscopic imaging, step 106, and repeating the registration and imaging procedure of steps 107 and 108, using the adjusted position of the pedicle screws as fiduciary markers. This procedure can be repeated iteratively until the desired position and orientation of the implanted configuration and the patient's orthopedic anatomy have been achieved. By using the implants as fiducial markers, the operator has an internal reference point which is an essential part of the instrumentation procedure.

Figure 2:
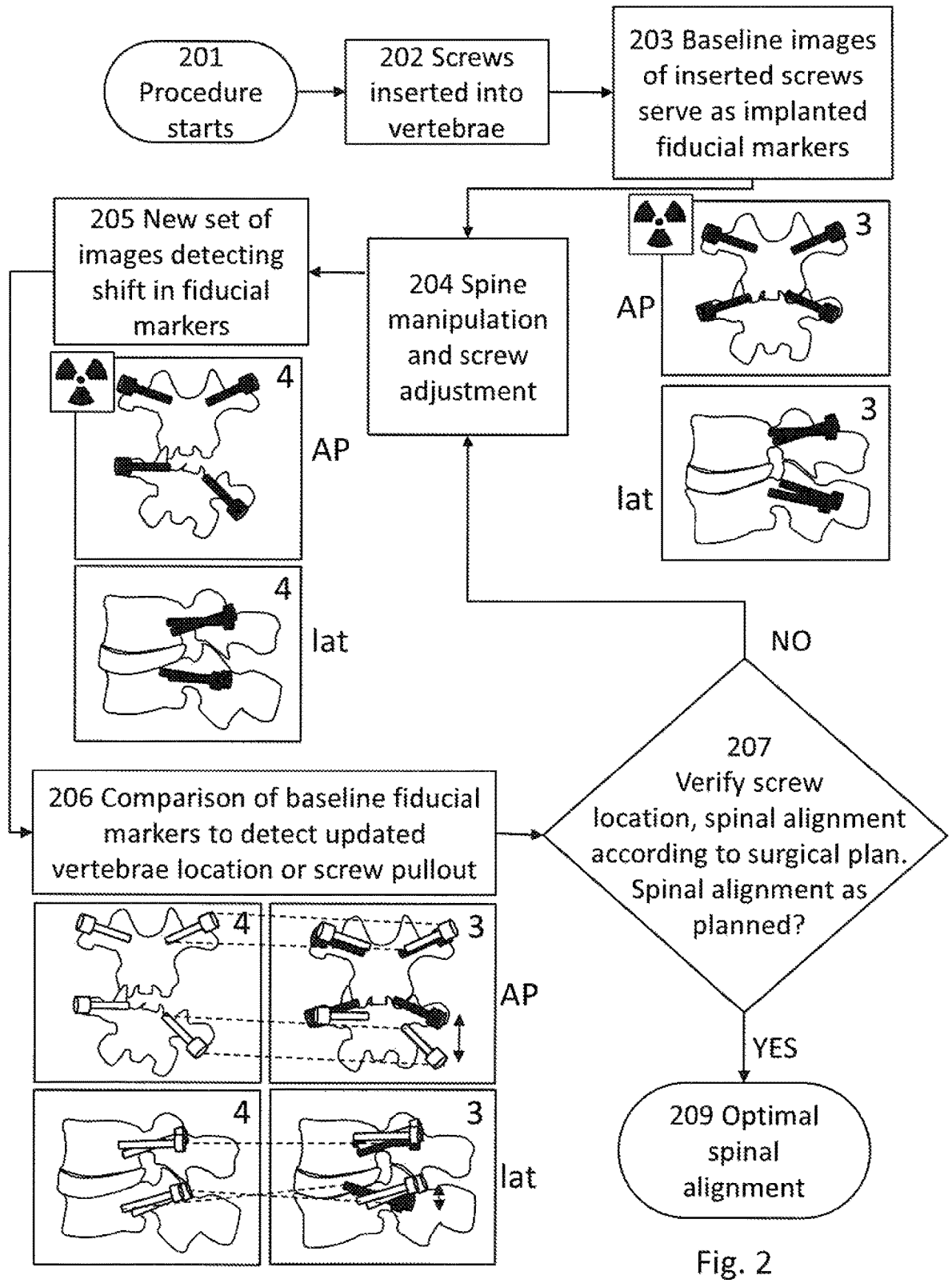
FIG. 2 illustrates details of the intra-operative iterative registration process for an operation requiring spinal manipulation as part of the surgical plan.

In FIG. 2, further details of the registration procedure itself are disclosed, illustrated as previously, for insertion of spinal fusion rods using pedicle screws. The surgical procedure begins in step 201. Screws are inserted into the vertebrae, often lumbar vertebrae L4 and L5, but in other implementations, different vertebrae or even different bones may be instrumented.

In step 203, a set of intraoperative images of the operated region of the spine, including the adjacent vertebrae and the implanted instrumentation, is acquired. These are the same images as set 3 from step 107 of FIG. 1. If using x-ray fluoroscopic images, both anterior-posterior (AP) and lateral (lat) images should be obtained. If using CT-fluoroscopy, a single 3D image is sufficient. These images (set 3) are compared with the previous set of images (set 2 from FIG. 1). Analysis of the images using image processing algorithms and software or visual image comparison, allows calculation of spinal alignment parameters and allows identification of any shift in the planned position of the pedicle screws. Based on this input, a decision is made regarding the need for manipulation of the patient's spinal alignment or the vertebral connecting rods.

These maneuvers are performed in step 204, and comprise at least one of physical movement of the patient's spine or the rods, and adjustment, replacement, removal, and insertion of any pedicle screws. Such maneuvers can involve the use of force, potentially placing strain on the implant system and the patient's bony anatomy. Such strain may result in dislocation of one or more implants from the bone they are intended to stabilize.

Thereafter, in step 205, a new set of intraoperative images (set 4) is obtained, with AP and lateral images generated. Only the pedicle screws are shown in the visualization of step 205, since they are the primary fiducial markers of the present example.

The alignment and registration procedure is then performed again in step 206, allowing detection of possible shifts in pedicle screw position and orientation, i.e., deviations from the pre-surgical plan, by comparing current position of the fiducial markers (set 4) with the position in the previous set of images (set 3) having the baseline pedicle screw position.

The purpose of this registration and analysis is to detect any deviations that could result in pull out of screws or mis-positioning that would endanger vital organs, result in an unstable implant configuration, or other aberration that would decrease the success of the procedure. Because the imaging procedure relies on fiducial markers that are an intrinsic part of the instrumentation procedure, and because these markers such as pedicle screws are clearly delineated and having a dense, three-dimensional radiopaque composition, the accuracy is potentially greater and margin of error less than a method relying on the use of fluoroscopically imaged anatomical features.

In step 207, a decision is made regarding the success of the alignment and position of the pedicle screws and correction of the spinal parameters as desired. If all alignments are according to the pre-surgical plan, the operation would be completed with optimal spinal alignment in step 208. If deviations or misplacement of the hardware is found, the operator has the option of returning to step 204 and carrying out additional iterative correctional manipulations.

Figure 3:
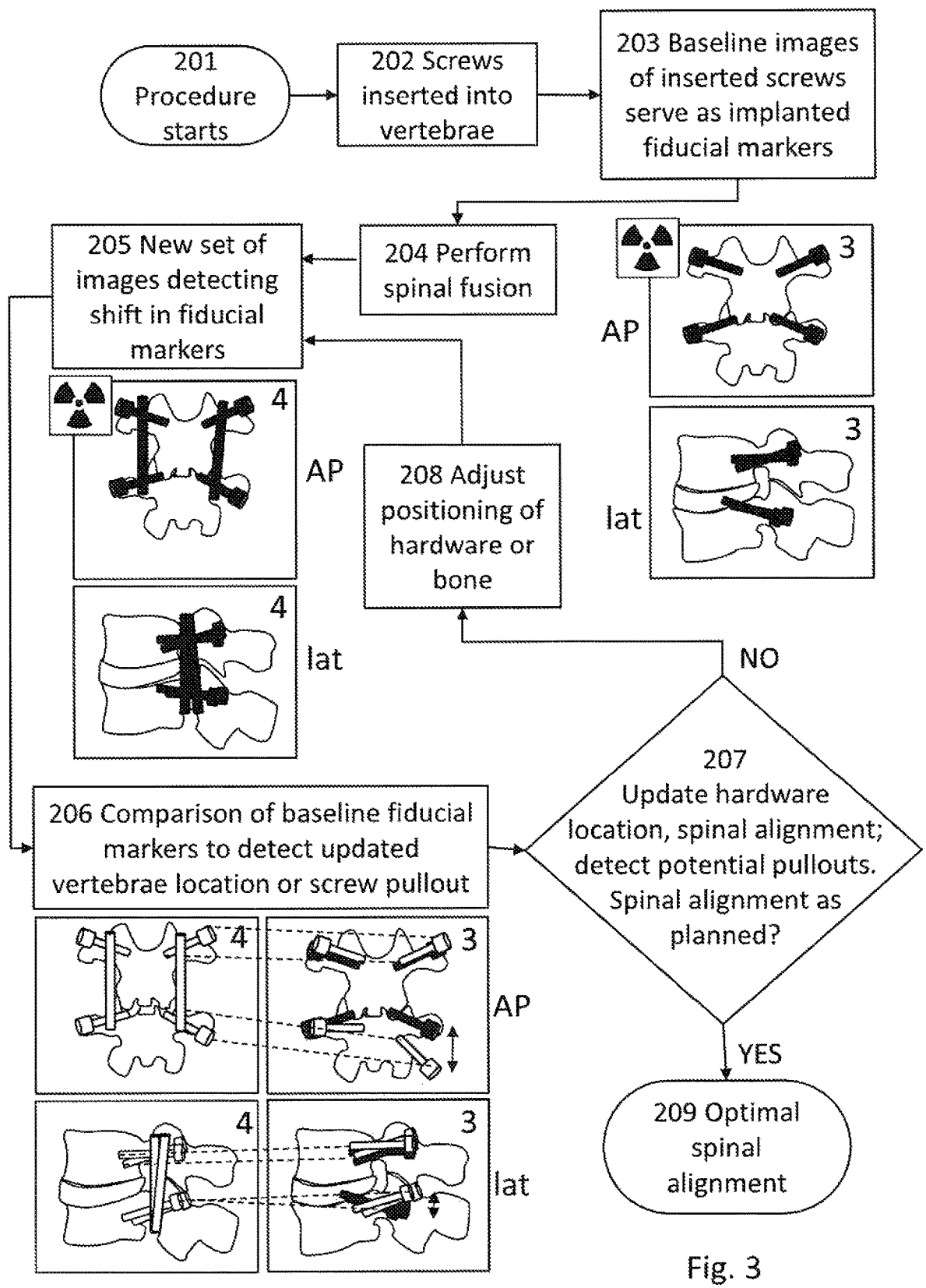
FIG. 3 illustrates details of the intra-operative registration process for verifying the position of inserted implants, using a spinal fusion as an exemplary embodiment.

Reference is now made to FIG. 3, showing an alternative implementation of the registration procedure. The steps are as illustrated in FIG. 2, except that a bony fusion procedure is performed in step 204 without requiring a specific step for spinal manipulation to correct deviations in alignment. In this case, the subsequent registration procedure is for the purpose of verifying that the bone-implant system is correctly positioned according to the preoperative plan. In this implementation, an additional step 208 has been added to allow for adjustment of hardware or bone positioning that deviates from the surgical plan, after the main surgical procedure has been performed. The difference between this and the process described in FIG. 2, is that the registration procedure is used for verification rather than being an integral part of the spinal manipulation. In the methods of both FIGS. 2 and 3, the procedure allows the surgeon to view exact positioning of implants relative to the bones, and have greater confidence in the successful completion of the operation.

In other implementations of the method, implanted rods, vertebral interbodies, or other components of the instrumentation may be used as fiducial markers. Any three-dimensional, radio-dense component of the implant system may be suitable for this purpose. The principle of the invention may also be applied to other orthopedic operations in which screws, plates, rods or other inserts are used to stabilize or correct a bony fracture. Furthermore, where orthopedic features are well defined and radio-dense, they can also be used as fiduciary registration features for ascertaining the accuracy of successive orthopedic surgical manipulations. Variations on the disclosed registration procedure may also be used in procedures in which metal or other radiopaque staples or inserts are used.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A registration method comprising:
   (a) acquiring a set of preoperative images of at least a surgical site of a subject to which a preoperative surgical plan relates, the preoperative surgical plan showing a planned position of implants on images of the surgical site;
   (b) acquiring a first at least one intraoperative image of the surgical site;
   (c) registering the first at least one intraoperative image with the set of preoperative images showing the planned position of implants, such that the planned position of implants is virtually imposed on the first at least one intraoperative image;
   (d) acquiring a second at least one intraoperative image showing a position of previously inserted implants, the previously inserted implants being physically inserted into the subject for causing a change to a bony region of the subject according to the preoperative surgical plan;
   (e) registering the second at least one intraoperative image showing the previously inserted implants from step (d) with the first at least one intraoperative image from step (c) using the previously inserted implants as fiducial markers;
   (f) verifying the position of the previously inserted implants inserted according to the preoperative surgical plan in further intraoperative images, using the registration from step (e); and
   (g) repeating at least some of steps (d) to (f) until the preoperative surgical plan is achieved.

2. The method of claim 1, wherein the surgical site includes a region of a spine, and the previously inserted implants used for the fiducial markers include pedicle screws.

3. The method of claim 1, wherein the surgical site includes a region of a spine, and the previously inserted implants used for the fiducial markers include connecting rods.

4. The method of claim 1, wherein the surgical site includes a region of a spine, and the previously inserted implants used for the fiducial markers include vertebral interbodies.

5. The method of claim 1, wherein the fiducial markers include any three-dimensional, radio-dense implant of the previously inserted implants.

6. The method of claim 1, wherein the fiducial markers include radiodense staples of the previously inserted implants.

7. The method of claim 1, wherein the surgical site includes the bony region of the subject.

8. The method of claim 1, wherein the set of preoperative images are acquired by at least one of CT and MRI.

9. The method of claim 1, wherein the first at least one intraoperative image comprises a first pair of two dimensional images.

10. The method of claim 9, wherein the second at least one intraoperative image comprises a second pair of two dimensional images, wherein each of the first pair and the second pair of two dimensional images show anterior-posterior and lateral views of the surgical site.

11. The method of claim 1, wherein the first or second at least one intraoperative image includes a single three-dimensional image acquired by CT-fluoroscopy.

12. A registration system, comprising:
a computer that executes a computer-executable algorithm to:
(a) acquire a set of preoperative images of at least a surgical site of a subject to which a preoperative surgical plan relates, the preoperative surgical plan showing a planned position of implants on images of the surgical site;
(b) acquire a first at least one intraoperative image of the surgical site;
(c) register the first at least one intraoperative image with the set of preoperative images showing the planned position of implants, such that the planned position of implants is virtually imposed on the first at least one intraoperative image;
(d) acquire a second at least one intraoperative image showing a position of previously inserted implants, the previously inserted implants being physically inserted into the subject to cause a change to a bony region of the subject according to the preoperative surgical plan;
(e) register the second at least one intraoperative image showing the previously inserted implants from step (d) with the first at least one intraoperative image from step (c) using the previously inserted implants as fiducial markers;
(f) verify the position of the previously inserted implants inserted according to the preoperative surgical plan in further intraoperative images, using the registration from step (e); and
(g) repeat at least some of steps (d) to (f) until the preoperative surgical plan is achieved.

13. The system of claim 12, wherein the surgical site includes a region of a spine, and the previously inserted implants used for the fiducial markers include pedicle screws.

14. The system of claim 12, wherein the surgical site includes a region of a spine, and the previously inserted implants used for the fiducial markers include connecting rods.

15. The system of claim 12, wherein the surgical site includes a region of a spine, and the previously inserted implants used for the fiducial markers include vertebral interbodies.

16. The system of claim 12, wherein the fiducial markers include any three-dimensional, radio-dense implant included of the previously inserted implants.

17. The system of claim 12, wherein the fiducial markers include radiodense staples of in the previously inserted implants.

18. The system of claim 12, wherein the surgical site includes the bony region of the subject.

19. The system of claim 12, wherein the set of preoperative images are acquired by at least one of CT and MRI.

20. A registration system, comprising:
a computer that executes a computer-executable algorithm to:
(a) acquire a set of preoperative images of at least a surgical site of a subject to which a preoperative surgical plan relates, the preoperative surgical plan showing a planned position of implants on images of the surgical site;
(b) acquire a first at least one intraoperative image of the surgical site, wherein the first at least one intraoperative image comprises a first pair of two dimensional images;
(c) register the first at least one intraoperative image with the set of preoperative images showing the planned position of implants, such that the planned position of implants is virtually imposed on the first at least one intraoperative image;
(d) acquire a second at least one intraoperative image showing a position of previously inserted implants, the previously inserted implants being physically inserted into the subject for causing a change to a bony region of the subject according to the preoperative surgical plan, wherein the second at least one intraoperative image comprises a second pair of two dimensional images;
(e) register the second at least one intraoperative image showing the previously inserted implants from step (d) with the first at least one intraoperative image from step (c) using the previously inserted implants as fiducial markers;
(f) verify the position of the previously inserted implants inserted according to the preoperative surgical plan in further intraoperative images, using the registration from step (e); and
(g) repeat at least some of steps (d) to (f) until the preoperative surgical plan is achieved.

* * * * *